（12) United States Patent
Broglio et al.

(10) Patent No.: US 9,751,816 B2
(45) Date of Patent: Sep. 5, 2017

(54) METHOD FOR PRODUCING LIGHT UNSATURATED HYDROCARBONS

(71) Applicant: Braskem S.A., Camacari-BA (BR)

(72) Inventors: Maria Ignez Broglio, Sao Paulo (BR); Augusto Teruo Morita, Sao Paulo (BR); Roberto Werneck do Carmo, Sao Paulo (BR); Luis Felipe de Souza Tavares, Sao Paulo (BR); Bruno Maia Moreira, Sao Paulo (BR)

(73) Assignee: Braskem S.A., Camacari-BA (BR)

( * ) Notice: Subject to any disclaimer, the term of this patent is extended or adjusted under 35 U.S.C. 154(b) by 0 days.

(21) Appl. No.: 15/105,398

(22) PCT Filed: Dec. 17, 2013

(86) PCT No.: PCT/BR2013/000569
§ 371 (c)(1),
(2) Date: Jun. 16, 2016

(87) PCT Pub. No.: WO2015/089593
PCT Pub. Date: Jun. 25, 2015

(65) Prior Publication Data
US 2016/0318825 A1    Nov. 3, 2016

(51) Int. Cl.
*C07C 1/24*     (2006.01)
*C07C 1/20*     (2006.01)
*C07C 4/04*     (2006.01)
*C10G 9/00*     (2006.01)
*C10G 3/00*     (2006.01)

(52) U.S. Cl.
CPC .................. *C07C 1/24* (2013.01); *C07C 1/20* (2013.01); *C10G 3/40* (2013.01); *C10G 9/00* (2013.01); *C07C 2529/40* (2013.01); *C07C 2529/85* (2013.01); *C10G 2400/20* (2013.01); *C10G 2400/22* (2013.01)

(58) Field of Classification Search
CPC ................ C07C 1/24; C07C 1/20; C07C 4/04
USPC ................ 585/324, 327, 330, 639, 640, 652
See application file for complete search history.

(56) References Cited

U.S. PATENT DOCUMENTS

| 2005/0038304 A1 | 2/2005 | Van Egmond et al. |
| 2010/0206771 A1 | 8/2010 | Rothaemel et al. |
| 2011/0112314 A1 | 5/2011 | Chewter et al. |
| 2011/0112345 A1 | 5/2011 | Chewter et al. |

FOREIGN PATENT DOCUMENTS

WO    2013/004544 A1    1/2013

*Primary Examiner* — Thuan D Dang
(74) *Attorney, Agent, or Firm* — Duane Morris LLP

(57) ABSTRACT

The present invention relates to a process of producing partly renewable light unsaturated hydrocarbons, in which at least one pyrolysis furnace of a unit for producing light unsaturated hydrocarbons from hydrocarbons is replaced by at least one reactor for conversion of ethanol to light unsaturated hydrocarbons.

15 Claims, 5 Drawing Sheets

METHOD FOR PRODUCING LIGHT UNSATURATED HYDROCARBONS

FIELD OF THE INVENTION

The present invention relates to a combined process for producing light unsaturated hydrocarbons, which enables gradual implantation of a process based on renewable raw material by using the nameplate capacity of petrochemical centrals. The combined process further enables gradual replacement of petrochemical raw material upon replacing cracking furnaces by units for converting ethanol of renewable origin chiefly into light unsaturated hydrocarbons, while keeping the whole conditioning and purifying area. The end products of the combined process, such as ethene, propene and C4s, exhibit content of modern carbon that roves lower emission of $CO_2$ per kilogram of product produced, as compared to those produced by means of a conventional petrochemical process.

DESCRIPTION OF THE PRIOR ART

Light unsaturated hydrocarbons like ethene and propene constitute important chemical platforms for producing a wide variety of products. Most of the production of these hydrocarbons is intended for generation of polymers. Vinyl chloride, ethylene oxide, propylene oxide and acrylonitrile are examples of other derivatives of light unsaturated hydrocarbons of great important in the chemical industry.

Conventionally, ethene is obtained from petrochemical processes, chiefly by steam cracking of petrochemical naphtha or ethane. Propene is obtained chiefly as a co-product from the production of ethene by steam cracking and from the production of gasoline from oil refinement.

The interest in the production of propene as the main product is increasing, since the growth of the demand for this olefin has exceeded the supply thereof from the production of ethene and of oil refinement. The migration to light raw materials on crackers in the USA as a result of the accelerated growth of the production of shale, as well as the rapid development of the production of ethene based on ethane in the Middle East, have been partly responsible for the deficit in the supply of propene.

As a result, alternative technologies for the production of propene have been developed, such as dehydrogenation of propene, metathesis of unsaturated hydrocarbons, interconversion of unsaturated hydrocarbons C4 and C5 and production of unsaturated hydrocarbons from methanol.

Alternatively, light unsaturated hydrocarbons may also be obtained from renewable sources. The interest in the use of products obtained from renewable sources over those obtained from fossil sources has been increased significantly, especially for polymers, since the replacement constitutes a viable manner of reducing the emission of gases that cause greenhouse effect.

Among the pathways of obtaining unsaturated hydrocarbons from renewable sources is the conversion of bioethanol, especially to ethene.

The term bioethanol refers to ethanol produced by fermenting at least one organic substrate from renewable natural raw materials, as for example, but not limited to, sugar-cane, maize, sorgo, wheat, lignocellulosic materials, among others. Throughout the text, bioethanol will be referred to only as ethanol.

Catalytic dehydration of ethanol to ethene was discovered by Priestley, in 1783 and first described in 1797 by Deiman et al. (Crell's Chem. Ann., vol. 2, p. 195-205, 310-316, 430-440, 1797). The first industrial plant for producing ethene from ethanol was launched still in the beginning of the Twentieth century and, as revised by A. Morschbacker in Bio-ethanol based ethylene (Journal of Macromolecular Science, Part C: Polymer Reviews, 2009), since then there has been many advances in the technologies of dehydrating ethanol to ethene.

Depending on the reaction conditions, including, but not limited to, catalyst type and temperature, the processes for obtaining unsaturated hydrocarbons by dehydrating ethanol may generate:
(i) chiefly ethene with small amounts of other co-products from secondary reactions, or still;
(ii) chiefly compositions of unsaturated hydrocarbons C2, C3 and C4 (butanes and occasionally 1,3-butadiene), besides other co-products from secondary reactions.

In case (ii), the composition of the mixture of unsaturated hydrocarbons may further be adjusted by additional processes in series: butene contents may be maximized by dimerization of the ethene and/or propene contents may be maximized by means of metathesis between ethene and butenes.

The production of light unsaturated hydrocarbons by dehydrating ethanol, in regions like Brazil, has a number of advantages, mainly the competitiveness ethanol obtained from sugar-cane, coupled to the low yield of carbon from the product resulting from the process (number of kilos of $CO_2$ that are emitted to the atmosphere during the manufacture of one kilo or product). Especially in Brazil, the existing mature sugar-alcohol industry supplies high production of fuel ethanol (anhydrous and hydrated) of high quality, within specifications regulated by the ANP (National Agency for Petroleum, Natural Gas and Biofuels), which may be advantageously employed as raw material for the production of olefins.

On the other hand, the dependency upon a raw material whose supply is associated to climatic variations and to other factors inherent in agricultural productions contributes significantly to the risks relating to the construction of a plant for producing unsaturated hydrocarbons based exclusively on ethanol in high production scales as those that are common in traditional petrochemical processes.

In a scenario that is unfavorable to petrochemical naphtha due to the loss of competitiveness with respect to ethanol, the present invention presents an alternative to the naphtha cracking units by replacing at least one pyrolysis furnace by at least one reactor for converting ethanol to olefins. Especially, the pathways for converting ethanol to light unsaturated hydrocarbons (C2, C3 and C4) have separation and purification steps that are similar to those existing at units for the production of olefins by cracking naphtha, according to the scheme in FIG. 1. Thus, the integration between the pathway of converting alcohol to light unsaturated hydrocarbons and an existing cracking unit proves to be an alternative to increase the economical return of the pathway.

The integration of oxygenate conversion process to olefins and steam cracking units has already been proposed, however in order to increase the production of light olefins:

In document US20050038304, the integration of a steam cracking unit with at least one MTO (methanol to olefin) reactor is proposed with a view of increasing the production of ethene and propene without adding an excessive load to the compression and fractioning equipment. However, the effect of the generation of co-products other than those obtained with the steam cracking process at the purifying steps and on the streams of product was not evaluated.

In document US20100206771, in order to overcome the low recovery of propene at a plant for steam cracking of ethane, the addition of at least one "methanol to olefins" reactor is proposed. According to the authors, the advantage of this process lies in making the production of ethene and propene flexible. In the example given, the addition of a methanol-to-propene reactor to increase the production of propene, but also to increase other by-products like gasoline and heavy hydrocarbons. A similar approach was presented in document US20110112314, in which, besides the integration between a "methanol-to-olefins" process with a steam cracking system, the document also proposes the synthesis of at least part of the methanol obtained by using the H2 co-produced on the cracker.

Document US20110112345 presents the integration between an oxygenates-to-olefins conversion system, with preferred feed comprising methanol or dimethyl ether, and a system for cracking light paraffins. In order to prevent overload in the separation and purification area, the cracking conditions are adjusted to guarantee low severity and high selectivity to ethene.

More recently, document WO2013004544 presented the addition of one or more ethanol-to-ethene reactors to a steam cracking plant to increase the production of ethene.

The processes reported in the literature that involve the integration of one or more oxygenates-to-olefins reactors to an existing petrochemical plant do not take into consideration the effect of the by-products generated by the additional reactor on the separation and purification area, especially for plants that are already at their maximum operating capacity.

In contrast, the present invention relates to the reduction of the feed of naphtha at an existing plant and to the replacement of petrochemical raw material by a renewable raw material by integration with one or more reactors for the conversion of ethanol to light hydrocarbons with no or little alteration in the separation and purification areas.

Besides presenting an alternative to the original raw material, while keeping the economical return of the plant, the present invention has, as a result, the reduction of emission of greenhouse effect gases on the production of olefins with the lowest possible investment, taking advantage of already existing actives. The present invention further enables gradual replacement of petrochemical raw material by renewable raw material, the increase in the profitability of the existing cracking unit, making the raw materials and the composition of products more flexible according to the market, besides eliminating bottlenecks of the existing plant for producing light unsaturated hydrocarbons by thermal cracking.

OBJECTIVES OF THE INVENTION

It is an objective of the present invention replacing at least one pyrolysis furnace of an existing plant for naphtha steam cracking with one or more reactors for converting ethanol to light unsaturated hydrocarbons.

It is another objective of the present invention reducing the use of raw material of fossil origin for the production of light unsaturated hydrocarbons by replacing it by a raw material of renewable origin, leading to the generation of partly renewable products.

It is a further objective of the present invention providing a flexible process that will enable gradual replacement of the raw material of fossil origin by raw material of renewable origin with the lowest cost possible.

It is still an objective of the present invention combining the naphtha steam cracking process with reactors for conversion of ethanol to light unsaturated hydrocarbons, promoting sharing of the largest possible number of pieces of equipment concerned with separation and purification of the product streams.

It is a further objective of the present invention providing a process that is flexible with regard to the ratio between light unsaturated hydrocarbons, enabling optimization of the production for products of higher value.

DETAILED DESCRIPTION OF THE INVENTION

Figure 1:
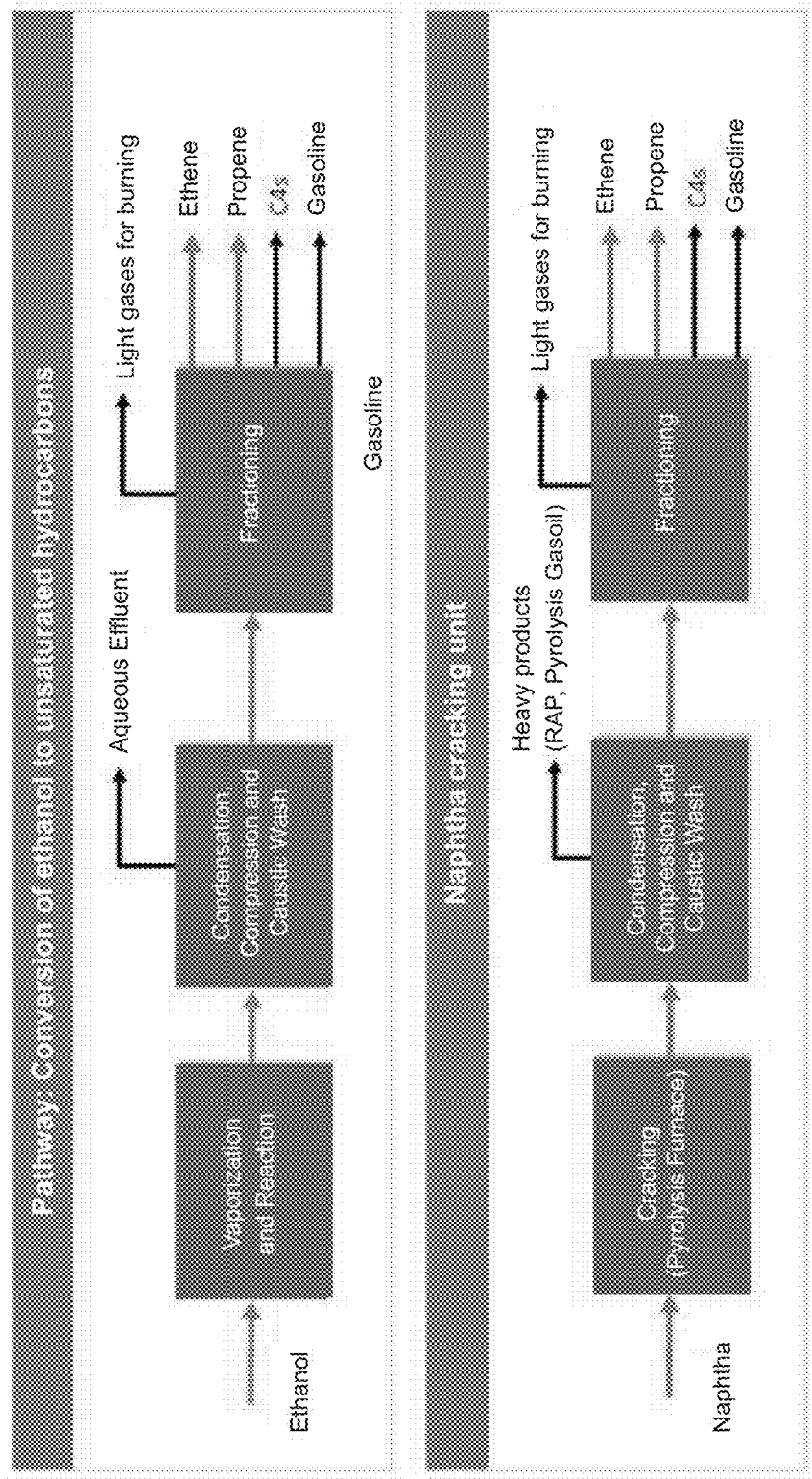
FIG. 1 shows a comparative generic scheme of the processes for converting ethanol to light unsaturated hydrocarbons, including a few co-products, and the cracking of naphtha.

The present invention relates to integration between the pathway for conversion of ethanol to light unsaturated hydrocarbons and an existing unit for cracking naphtha by replacing pyrolysis furnaces by reactors for converting ethanol to light unsaturated hydrocarbons. The integration enables gradual replacement of the cracking furnaces by reactors of conversion of ethanol to light unsaturated hydrocarbons, and the generation of partly renewable products.

Raw Materials

The stream of hydrocarbons of fossil origin used as raw material in the production of olefins by thermal cracking comprises hydrocarbons in the range from C2 to C40, preferably from C2 to C30, more preferably from C2 to C20, and still more preferably from C5 to C12, with boiling point of naphtha ranging from 36° C. to about 195° C.

The ethanol used in the present invention as feeding of the process for conversion of ethanol to light unsaturated hydrocarbons may be produced from, but not limited to, fermentation of at least one organic substrate coming from renewable natural raw materials, as for example, but not limited to, sugar-cane, maize, sorgo, wheat, lignocellulosic materials, among others, being preferably obtained from sugar-cane. Mixtures of ethanol from different sources may also be used in the present invention. The ethanol used in feeding the process for conversion of ethanol to light unsaturated hydrocarbons may be either hydrated ethanol or anhydrous, the fuel hydrated ethanol being preferably used.

Optionally, ethanol may be subjected to a purifying step prior to the step of converting it to light unsaturated hydrocarbons. The process employed for removing impurities from the ethanol load may be either a system of porous membranes or adsorption bed or a system composed by vessels with ion-exchange resins, or an assembly that employs two or more of the systems cited. Preferably, the system is composed by vessels with ion-exchange resins.

Points of Integration

The points of integration between the pathway for conversion of ethanol to light unsaturated hydrocarbons and the existing naphtha cracking unit are defined according to the following aspects:

(a) composition of the reaction product from the process for conversion of ethanol to light unsaturated hydrocarbons;
(b) composition of the reaction product from cracking, determined by the severity of the pyrolysis furnaces and of the composition of the raw material used;
(c) available equipment and the respective dimensions thereof;
(d) loads of the compression system; and
(e) existence of bottlenecks at the plant.

In a first embodiment, the present invention relates to a process for the production of partly renewable light unsaturated hydrocarbons, in which at least one pyrolysis furnace of a unit for the production of light unsaturated hydrocarbons from hydrocarbons is replaced by at least one reactor for conversion of ethanol to light unsaturated hydrocarbons, wherein:

(a) ethanol is contacted with an acidic catalyst in at least one reactor under conditions suitable to form a stream of reaction effluent comprising water, ethene, propene and unsaturated hydrocarbons with four carbon atoms, besides other co-products from secondary reactions;
(b) the stream generated in (a) is fed to a cooling unit by direct contact under conditions suitable to form a top stream containing most of the light unsaturated hydrocarbons present in the stream of effluent from step (c) and a bottom stream containing most of the water present in the stream of effluent from step (a);
(c) the top stream rich in light unsaturated hydrocarbons generated in b) is compressed;
(d) naphtha is contacted with steam in a pyrolysis furnace under conditions suitable to form a stream of effluent from the cracking comprising light unsaturated hydrocarbons, fuel oil, gas oil and gasoline;
(e) the effluent generated in the cracking reaction (d) is separated into a stream of light hydrocarbons containing most of the light unsaturated hydrocarbons present in the effluent of step (d) and at least one stream of heavy hydrocarbons;
(f) the stream rich in light unsaturated hydrocarbons from step (e) is fed to a direct-contact cooling unit under conditions suitable to form a top stream containing most of the light unsaturated hydrocarbons present in the effluent from reaction (e) and a bottom stream containing the condensed compounds and most of the water present in the effluent from reaction (d);
(g) the top stream rich in unsaturated hydrocarbons generated in (f) is compressed;
(h) the streams (c) and (g) are combined and led to the steps of separating and purifying unsaturated hydrocarbons C2, C3 and C4 from the existing cracking unit.

In a preferred embodiment, the present invention relates to a process for producing partly renewable light unsaturated hydrocarbons as described above, in which the top stream generated in step (b) is contacted with a base solution at a caustic wash unit under conditions suitable for removing at least a part of $CO_2$ from the stream before being compressed in step (c).

In a preferred embodiment, the present invention relates to a process for producing partly renewable light unsaturated hydrocarbons as described above, in which the top stream generated in step (f) is contacted with a base solution in a caustic wash unit under conditions suitable to remove at least a part of $CO_2$ from the stream before being compressed in step (g).

In a preferred embodiment, the present invention relates to a process for producing partly renewable light unsaturated hydrocarbons, in which the stream combined in step (h) is contacted with a base solution in a caustic wash unit under conditions suitable to remove at least a part of $CO_2$ from the stream before being sent to the steps of separating and purifying unsaturated hydrocarbons, C2, C3 and C4 of the existing cracking unit.

In a second embodiment, the present invention relates to a process for producing partly renewable light unsaturated hydrocarbons, wherein at least one pyrolysis furnace of a unit for producing light unsaturated hydrocarbons from hydrocarbons is replaced by at least one reactor for conversion of ethanol to light unsaturated hydrocarbons, in which:

(a) ethanol is contacted with an acid catalyst in at least one reactor under conditions suitable to form a stream of reaction effluent comprising water, ethene, propene and unsaturated hydrocarbons with four carbon atoms, besides other co-products of secondary reactions;
(b) the stream generated in (a) is fed in a direct-contact cooling unit under conditions suitable to form a top stream containing most of the light unsaturated hydrocarbons present in the effluent stream from step (a) and a bottom stream containing most of the water present in the effluent stream from step (a);
(c) naphtha is contacted with steam in a pyrolysis furnace under conditions suitable to form a cracking effluent stream comprising light unsaturated hydrocarbons, fuel oil, gas oil and gasoline;
(d) the effluent generated in the cracking reaction (c) is separated into a light unsaturated hydrocarbon stream containing most of the light unsaturated hydrocarbons present in the effluent from step (c) and at least a heavy hydrocarbon stream;
(e) the stream rich in light unsaturated hydrocarbons from step (d) is fed to a direct-contact cooling unit under conditions suitable to form a top stream containing most of the light unsaturated hydrocarbons present in the effluent of reaction (d), and a bottom stream containing the condensed compounds and most of the water present in the effluent from reaction (c);
(f) the streams (b) and (e) are combined and contacted with a base solution in a caustic wash unit under conditions suitable to remove at least a part of $CO_2$ from the stream and sent to the steps of separating and purifying unsaturated hydrocarbons C2, C3 and C4 of the existing cracking unit.

In a third embodiment, the present invention relates to a process for producing partly renewable light unsaturated hydrocarbons, in which at least one pyrolysis furnace of a unit for production of light unsaturated hydrocarbons from hydrocarbons is replaced by at least one reactor for conversion of ethanol to light unsaturated hydrocarbons, in which:

(a) ethanol is contacted with an acid catalyst in at least one reactor under conditions suitable to form a reaction effluent stream comprising water, ethene, propene and unsaturated hydrocarbons with four carbon atoms, besides other co-products from secondary reactions;

(b) naphtha is contacted with steam in a pyrolysis furnace under conditions suitable to form a cracking effluent stream comprising light unsaturated hydrocarbons, fuel oil, gas oil and gasoline;

(c) the effluent generated in the cracking reaction (c) is separated into a light unsaturated hydrocarbon stream containing most of the light unsaturated hydrocarbons present in the effluent of step (c) and at least one heavy hydrocarbon stream;

(d) the effluent stream from the step of converting ethanol to unsaturated hydrocarbons (a) and the light unsaturated hydrocarbons generated in (c) are combined prior to the direct-contact cooling step to remove condensates and water, followed by contact with a base solution in a caustic wash unit under conditions suitable to remove at least a part of $CO_2$ from the stream and from the steps of separating and purifying unsaturated hydrocarbons C2, C3 and C4 from the existing cracking unit.

The descriptions have the objective of exemplifying the integrations proposed for replacing at least a part of the raw material of fossil origin by the raw material of renewable origin (ethanol). For this purpose, it is described, in a general manner, the processes for cracking naphtha and converting ethanol to light unsaturated hydrocarbons, just by way of example of the embodiments of the invention, without limiting it.

Figure 2:
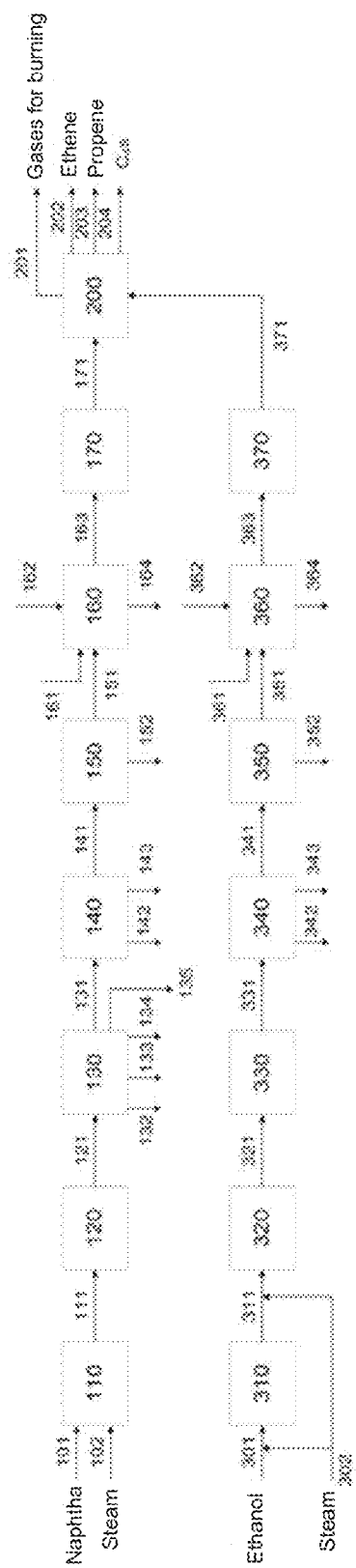
FIG. 2 shows a scheme of the integration between processes for converting ethanol to light unsaturated hydrocarbons and for cracking naphtha, sharing the olefin separation and purification system.

In an embodiment, the integration between the pathway of converting ethanol to light unsaturated hydrocarbons and the existing naphtha cracking unit is made by sharing the olefin separating and purifying systems, as can be observed in FIG. 2. This embodiment is preferred when there is a pressure difference in the feedings of the compressors of the two processes.

Naphtha (101) is heated, vaporized and diluted with low-pressure steam (102) for cracking reaction. The stem/hydrocarbons ratio at the inlet of the pyrolysis furnaces depends on the composition of the raw material and usually ranges from 0.3 to 1.

In the pyrolysis furnace (110) the reaction takes place by action of the temperature (about 850° C.) and the naphtha is transformed into light olefins, fuel oil, gas oil and gasoline (111). Part of the heat supplied to the furnaces for cracking reaction is recovered for cracking and vaporizing naphtha and for generating steam for consumption at the plant.

The system for cooling the stream coming out of the furnaces is optionally composed by: direct-contact cooling ion heat exchangers, making use of the heat for generating high-pressure steam (120); then, by direct contact with oil (130), where the fuel (132), gasoil (133), heavy fraction of gasoline (134) and residual coke (135) are separated as by-products; and finally the stage of condensation by direct contact with water or air (140), wherein light fraction of gasoline (142) and aqueous effluent (143) are generated as by-products.

The gas from the quench tower (141) is compressed by multiple-stage compressors (150) under a pressure suitable for cryogenic distillation, wherein a condensate stream (152) is generated as by-product. The pressure of the condensate stream preferably ranges from 1500 to 3000 KPa (15 to 30 bar) and still more preferably from 1800 to 2600 kPa (18 to 26 bar).

After compression, the acid gases (H2S, CO2, COS, CS2) are removed by contact with a base solution (162) and the process water (161) in a caustic wash unit (160), where aqueous affluent (164) is generated as by-product. Optionally, a few stages of the compression may take place after the caustic wash step.

The residual water is removed by contact with adsorption beds with desiccating agents (170) prior to the step of separation and purification by fractioning.

For the reaction of converting ethanol to light unsaturated hydrocarbons, ethanol (301) is heated, vaporized and overheated in multiples furnaces (310) by means of integrations with the out-coming stream of the dehydration reaction.

The reaction system is optionally composed by multiple reactors (320) and multiple furnaces (310). The process may be conducted either in the isothermal or in the adiabatic modes.

In adiabatic systems, one may optionally add an amount of steam or water or another inert material with high calorific value (302) so as to reduce the drop in the temperature in the reactor. If the inert material is water, its total massic concentration at the reactor inlet may range from 5 to 80%, preferably from 25 to 70% and more preferably from 45 to 65%.

The catalyst employed in the reaction of converting ethanol to light unsaturated hydrocarbons may be any acid catalyst capable of converting ethanol chiefly in a composition comprising unsaturated hydrocarbons C2, C3 e C4. The unsaturated hydrocarbons C4 may comprise 1,3-butadiene besides 1 and 2-butenes, 2-butenes being a mixture of the cis and trans isomers. As examples, one can cite zeolites, silica-alumina, silico-aluminum-phosphates, aluminosilicates, besides other metallic oxides and variations of the catalysts cited modified with metals and/or phosphor, as well as the mixture of two or more thereof. The products obtained (321) are similar to those produced by cracking naphtha: ethene, propene, mixture of hydrocarbons with four carbon atoms, aromatics and others (including heavy hydrocarbons containing 5 or more carbon atoms). The reaction products of the conversion of ethanol to unsaturated hydrocarbons should exhibit in their composition (dry base) from 15 to 60% by mole of ethene, from 5 to 40% by mole of propene and from 3 to 35% by mole of C4, C4 being a mixture of 1 and 2-butenes and optionally 1,3-butadiene.

The reaction of converting ethanol to unsaturated hydrocarbons takes place at temperatures ranging from 400 to 800° C., preferably from 400 to 600° C. and under pressures ranging from 100 to 2000 kPa (1 to 20 bar).

The gas from the reaction (321) is cooled by integrations with the in-coming stream (330) and fed to a water quench tower (340), in order to condense most of the water present in the stream, wherein hydrocarbons for burning (342) and aqueous effluent (343) are generated as by-products.

The gas from the quench tower (341) is compressed ion multiple-stage compressor (350) under a pressure suitable to be fed to the purifying system, which already exists at the naphtha cracking plant, wherein a condensate stream (352) is generated as by-product. The pressure of the condensate stream preferably ranges from 1500 to 3000 kPa (15 to 30 bar) and still more preferably from 1800 to 600 kPa (18 to 26 bar).

After compression, it is removed, by contact with a base solution (362) and process water (361) in a caustic wash unit (360), the CO2 and organic acids generated in the reaction, wherein aqueous effluent (364) is generated as by-product. Optionally, a few compression stages may take place after the caustic wash step.

The residual water is removed from the gaseous product from the caustic wash, for instance, by contact with adsorption beds with desiccating agent (370).

Figure 3:
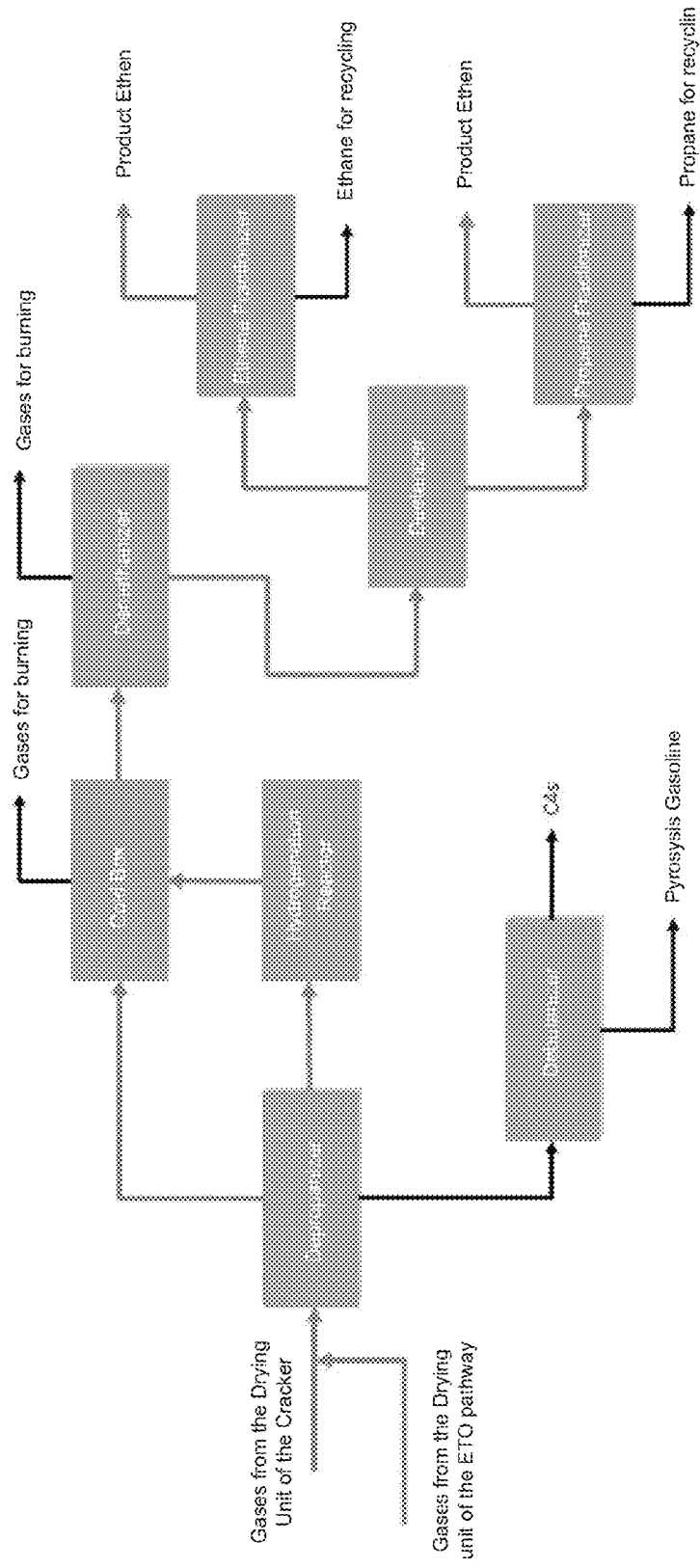
FIG. 3 shows a scheme exemplifying the separation and purification zones of plant for thermal cracking of petrochemical naphtha shared in the integration of FIG. 2.

The gases from the drying of the pathway of conversion of ethanol to light unsaturated hydrocarbons (371) and the cracking (171) are combined and fed in an olefin separation and purification system (200). There are various possible configurations for the arrangement of the distillation columns in separating and purifying olefins, all of them being compatible with the integration. As an example, a system presented in FIG. 3 uses the depropanizing column in the beginning of the separation and purification area.

The bottom products of the depropanizing column are fed to a debutanized column, in which a stream of product comprising a mixture of C4s and a stream rich in C5 and C6 are separated, and the latter may be specified as pyrolysis gasoline.

The distillate stream from the depropanizer passes through a hydrogenation reactor (hydrogenation of acetylenes) and is fed to the cold area together with the top gases from the depropanizer.

In the cold area, hydrogen and a part of the methane are separated and sent to burning, while the rest of methane is separated in the demetanizing column.

The bottom of the demethaniziner is fed to the deethanizer. The top product from the deethanizer is fed to the ethene fractioning column, from where the ethene product is obtained, and the bottom product of the deethanizer is fed to the propene fractioning column, from where the propene product is obtained.

Figure 4:
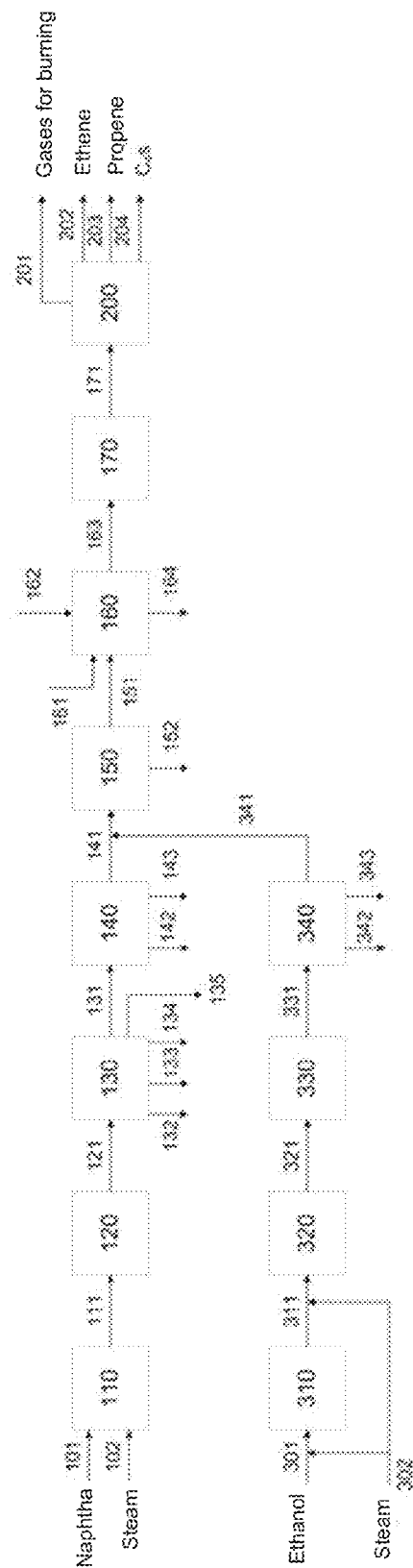
FIG. 4 shows a scheme of the integration between processes for converting ethanol to light unsaturated hydrocarbons and for cracking naphtha, sharing the separation and purification system, caustic wash, drying and compression.

In another embodiment, the integration is carried out by sharing the system of separating and purifying olefins, caustic wash, drying and compression, as shown in FIG. 4. This embodiment is preferred when there is a bottleneck at the quench tower due to the excess water at the inlet of the process of converting ethanol to unsaturated hydrocarbons with respect to the cracking.

Figure 5:
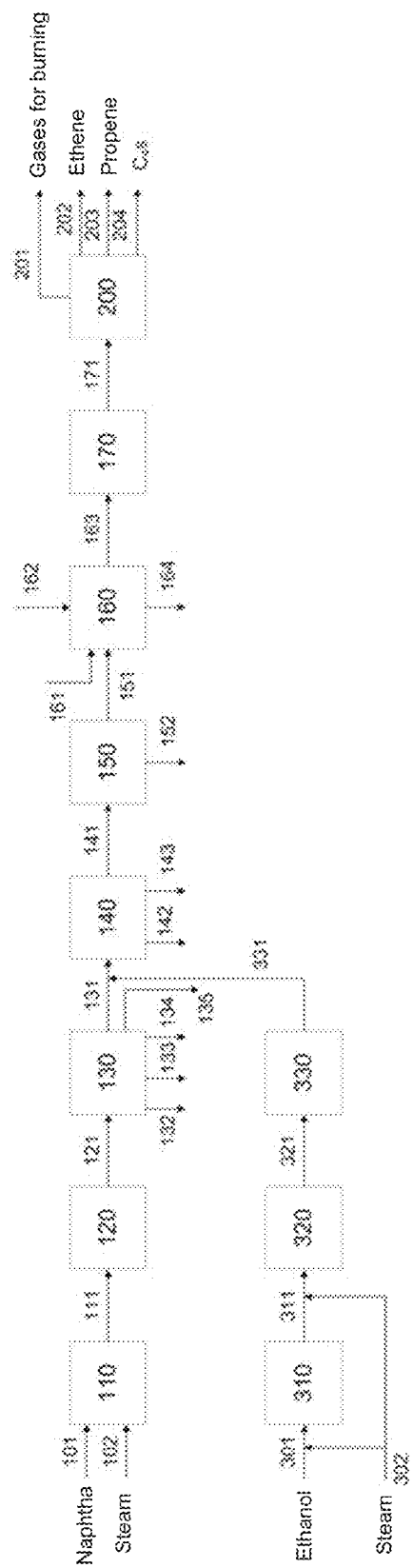
FIG. 5 shows a scheme of the integration between processes for converting ethanol to light unsaturated hydrocarbons and for cracking naphtha, sharing the separation and purification system, caustic wash, drying, compression and water quench.

In another embodiment, the integration is carried out by sharing the system of separating and purifying olefins, caustic wash, drying, compression and water quench, as shown in FIG. 5. This embodiment uses the smallest number of pieces of equipment possible and, since it requires less investment, it is preferred when no piece of equipment is the bottleneck.

Comparative Example 1

A typical ethanol-to-olefin conversion plant was evaluated in terms of the investment necessary for the construction thereof, including units necessary to store raw materials and products, besides units for providing facilities and treatment of effluents. The distribution of investment is shown in Table 1.

TABLE 1

Distribution of investment for the construction of a typical ethanol-to-olefin conversion plant

| Investment component | % |
|---|---|
| Reaction and vaporization | 10 |
| Quench, compression and caustic wash | 13 |
| Separation and purification of ethene | 15 |
| Separation and purification of propene | 9 |
| Separation of butenes | 6 |
| Provision of utilities | 23 |
| Treatment of effluents | 7 |
| Storage (raw material and products) | 17 |

Example 1

The investment necessary to the construction of an ethanol-to-olefin conversion plant was estimated by considering the integration with a pre-existing naphtha cracking plant, as shown in FIG. 4. In this embodiment, it is assumed total sharing of the systems for separating and purifying olefins (ethene, propene and butenes) and of units for providing facilities of the cracking plant. Besides, it is assumed the investment for the construction of a unit for storing raw material (ethanol). On the basis of comparative example 1, the percentage reduction of investment in the conditions of sharing described would reach about 60%.

Example 2

Contents (% by Mass) of Ethene and Renewable Propene in the Ethene and Propene Streams of Example 2 for Three Different Ethanol Conversion Catalysts Table 2 shows a product composition typical for naphtha cracking and compositions of conversion of ethanol to unsaturated hydrocarbons obtained experimentally with three different catalysts. From these compositions, it is calculated the mass contents of renewable ethene and propene produced by replacing 10% of the feed of raw petrochemical raw material (naphtha) by renewable raw material (ethanol) for three compositions of effluent from the ethanol conversion reactor corresponding to the three catalysts, considering a naphtha cracking plant with production capacity of 870 kta of light olefins (ethene and propene).

TABLE 2 out-coming compositions typical of naphtha cracking furnace and out-coming compositions of reactor for conversion of ethanol to unsaturated hydrocarbons using three different catalysts.

| | Naphtha | Zr-ZSM-5 | SAPO-34 | ZSM-5 |
|---|---|---|---|---|
| H2 | 0.10883 | 0.00023 | 0.00510 | 0.01315 |
| CO | 0.00181 | 0.00473 | 0.01527 | 0.00026 |
| CO2 | 0.00060 | 0.00115 | 0.00391 | 0.00026 |
| Methane | 0.29021 | 0.00620 | 0.00394 | 0.00684 |
| Acetylene | 0.00605 | — | — | — |
| Ethylene | 0.30834 | 0.53067 | 0.44593 | 0.52590 |
| Ethane | 0.05441 | 0.01007 | 0.00185 | 0.00789 |
| Propene | 0.09674 | 0.32021 | 0.40458 | 0.21912 |
| Propane | 0.00605 | 0.00735 | 0.00838 | 0.01753 |
| C4 | 0.05441 | 0.11105 | 0.10114 | 0.19984 |
| C5 | 0.01209 | 0.00001 | 0.00009 | 0.00657 |
| C6 | — | 0.00001 | — | — |
| BTX | 0.05441 | 0.00365 | 0.00232 | — |
| Fuel oil | 0.00605 | — | — | — |
| Ethanol | — | 0.00468 | 0.00113 | 0.00132 |
| Diethyl ether | — | — | 0.00636 | 0.00132 |

TABLE 3

Contents of renewable ethene and propene with replacement of 10% of the naphtha feed by ethanol

| Catalyst for conversion of ethanol to unsaturated HCs | Production kg/h | % of renewable ethene | renewable kg/h | % production propene |
|---|---|---|---|---|
| Base case (Naphtha) | 73491 | — | 34257 | — |
| ZSM-5 (Si/Al2 = 90) | 71365 | 6.8% | 35363 | 12.3% |
| Zr-ZSM-5 (Si/Al2 = 30) | 71743 | 7.3% | 38068 | 18.5% |
| SAPO-34 | 73103 | 10.4% | 35116 | 11.7% |

Example 3

Effect of Replacement of 10% of the Petrochemical Raw Material at the Separation and Purification Steps at a Plant with Capacity of 870 kta In order to evaluate the effect of replacing 10% (by mass) of the naphtha feeding by ethanol, according to the integration of FIG. 2, at a plant with production capacity of 870 kta of light olefins (ethene and propene) in the separation and purification steps it is calculated (Aspen Plus™) the relative heats involved in the condensation (∟Qc) and evaporation (∟Qn) in the main columns of steps of separating and purifying the light olefins (ethene and propene) with respect to the base case (naphtha). Considering the base case, from naphtha, there is a significant reduction in the heats required for the columns, bearing in mind that the olefin/paraffin relation in the process of converting ethanol to unsaturated hydrocarbons is significantly higher than that obtained from the naphtha cracking. Globally, for the cases presented, such a condition provides availability of the pieces of equipment installed in the separation and purification steps.

TABLE 4

Relative heats involved in the condensation (∟Qc) and evaporation (∟Qn) in the main columns of the steps of separating and purifying the light olefins (ethene and propene) with respect to the base case (naphtha)

| | ∟Qc (%) | ∟Qn (%) | ∟Flow rate (%) |
|---|---|---|---|
| H2 removal column | −9.5 | −9.5 | −8.0 |
| Methane removal column | −88.3 | −23.0 | −9.3 |
| Deethanizing column | −20.0 | −19.3 | −3.0 |
| Ethen purifying column | −20.6 | −16.4 | −2.0 |
| Propene purifying column | −59.1 | −59.5 | −5.64 |

What is claimed is:

1. A process for producing partly renewable light unsaturated hydrocarbons, comprising:
   (a) contacting ethanol with an acid catalyst in at least one reactor under conditions suitable to form a reaction effluent stream comprising water, ethene, propene and unsaturated hydrocarbons with four carbon atoms, besides other co-products of secondary reactions;
   (b) feeding the stream generated in (a) to a direct-contact cooling unit under conditions suitable to form a top stream containing most of the light unsaturated hydrocarbons present in the effluent stream of step (a) and a bottom stream containing most of the water present in the effluent stream of step (a);
   (c) compressing the top stream rich in light unsaturated hydrocarbons generated in (b);
   (d) contacting naphtha with steam in a pyrolysis furnace of an existing cracking unit under conditions suitable to form a cracking effluent stream comprising light unsaturated hydrocarbons, fuel oil, gas oil and gasoline;
   (e) separating the effluent generated in the cracking reaction (d) into a light hydrocarbon stream containing most of the light unsaturated hydrocarbons present in the effluent of step (d) and at least one heavy hydrocarbon stream;
   (f) feeding the stream rich in light unsaturated hydrocarbons from step (e) to a direct-contact cooling unit under conditions suitable to form a top stream containing most of the light unsaturated hydrocarbons present in the effluent of reaction (e) and a bottom stream containing the condensed compounds and most of the water present in the effluent of reaction (d);
   (g) compressing the top stream rich in unsaturated hydrocarbons generated in (f);
   (h) combining the streams (c) and (g) and conducting them to the steps of separating and purifying unsaturated hydrocarbons C2, C3 and C4 of the existing cracking unit, wherein said pyrolysis furnace of said existing cracking unit is gradually replaced by reactors for conversion of ethanol to light unsaturated hydrocarbons.

2. The process according to claim 1, wherein the top stream generated in (b) is contacted with a base solution in a caustic wash unit under conditions suitable to remove at least part of the $CO_2$ from the stream before it is compressed in step (c).

3. The process according to claim 2, wherein the top stream generated in (f) is contacted with a base solution in a caustic wash unit under conditions suitable to remove at least part of the $CO_2$ from the stream before it is compressed ion step (g).

4. The process according to claim 1, wherein the stream combined in (h) is contacted with a base solution in a caustic wash unit under conditions suitable to remove at least part of the $CO_2$ from the stream before it is sent to the steps of separating and purifying unsaturated hydrocarbons C2, C3 and C4 of the existing cracking unit.

5. The process according to claim 1, characterized in that the stream of hydrocarbons of fossil origin used as raw material in the production of light unsaturated hydrocarbons comprises hydrocarbons in the range from C2 to C40.

6. The process according to claim 5, wherein the stream of hydrocarbons of fossil origin used as raw material in the production of light unsaturated hydrocarbons comprises hydrocarbons ranging from C2 to C30.

7. The process according to claim 6, wherein the stream of hydrocarbons of fossil origin used as raw material in the production of light unsaturated hydrocarbons comprises hydrocarbons ranging from C2 to C20.

8. The process according to claim 7, wherein the stream of hydrocarbons of fossil origin used as raw material in the production of light unsaturated hydrocarbons comprise hydrocarbons ranging from C5 to C12 with boiling point of naphtha ranging from about 36° C. to about 195° C.

9. The process according to claim 1, wherein the ethanol used as raw material for the process of converting ethanol to light unsaturated hydrocarbons is obtained by fermenting at least one organic substrate from renewable natural raw materials.

10. The process according to claim 9, wherein the ethanol used as raw material for the process of converting ethanol to light unsaturated hydrocarbons is either hydrated or anhydrous ethanol.

11. The process according to claim 10, wherein the ethanol used as raw material for the process of converting ethanol to light unsaturated hydrocarbons is fuel-grade hydrated ethanol.

12. The process according to claim 1, wherein the reaction products from the conversion of ethanol to unsaturated hydrocarbons exhibit, in their composition (on dry base), from 15 to 60% by mole of ethene, from 5 to 40% by mole of propene and from 3 to 35% by mole of C4, C4 being a mixture of 1 and 2-butenes.

13. The process according to claim 12, wherein the composition of C4 comprises a mixture of 1 and 2-butenes and 1,3-butadiene.

14. A process for producing partly renewable light unsaturated hydrocarbons, comprising:
   (a) contacting ethanol with an acid catalyst in at least one reactor under conditions suitable to form a reaction effluent stream comprising water, ethene, propene and unsaturated hydrocarbons with four carbon atoms, besides other co-products of secondary reactions;

(b) feeding the stream generated in (a) to a direct-contact cooling unit under conditions suitable to form a top stream containing most of the light unsaturated hydrocarbons present in the effluent stream of step (a) and a bottom stream containing most of the water present in the effluent stream of step (a);

(c) contacting naphtha with steam in a pyrolysis furnace of an existing cracking unit under conditions suitable to from a cracking effluent stream comprising light unsaturated hydrocarbons, fuel oil, gas oil and gasoline;

(d) separating the effluent generated in the cracking reaction (c) into a light unsaturated hydrocarbon stream containing most of the light unsaturated hydrocarbons present in the effluent of step (c) and at least one heavy hydrocarbon stream;

(e) feeding the stream rich in light unsaturated hydrocarbons from step (d) to a direct-contact cooling unit under conditions suitable to form a top stream containing most of the light unsaturated hydrocarbons present in the effluent of reaction (d) and a bottom stream containing the condensed compounds and most of the water present in the effluent of reaction (c);

(f) combining the streams (b) and (e) and contacting them with a base solution in a caustic wash unit under conditions suitable to remove at least a part of the $CO_2$ from the stream and sending them to the steps of separating and purifying unsaturated hydrocarbons C2, C3 and C4 of the existing cracking unit, wherein said pyrolysis furnace of said existing cracking unit is gradually replaced by reactors for conversion of ethanol to light unsaturated hydrocarbons.

15. A process for producing partly renewable light unsaturated hydrocarbons, comprising:

(a) contacting ethanol with an acid catalyst in at least one reactor under conditions suitable to form a reaction effluent stream comprising water, ethene, propene and unsaturated hydrocarbons with four carbon atoms, besides other co-products of secondary reactions;

(b) contacting naphtha with steam in a pyrolysis furnace of an existing cracking unit under conditions suitable to form a cracking effluent stream comprising light unsaturated hydrocarbons, fuel oil, gasoil and gasoline;

(c) separating the effluent generated in the cracking reaction (c) into a light unsaturated hydrocarbon stream containing most of the light unsaturated hydrocarbons present ion the effluent of step (c) and at least one heavy hydrocarbon stream;

(d) combining the effluent stream of the step of converting ethanol to unsaturated hydrocarbons (a) and the light unsaturated hydrocarbon stream generated in step (c) before the direct-contact fooling step for removal of condensates and water, followed by contact with a base solution in a caustic wash unit under conditions suitable to remove at least a part of the CO2 from the stream and from the steps of separating and purifying unsaturated hydrocarbons C2, C3 and C4 of the existing cracking unit, wherein said pyrolysis furnace of said existing cracking unit is gradually replaced by reactors for conversion of ethanol to light unsaturated hydrocarbons.

* * * * *